(12) United States Patent
Estevez

(10) Patent No.: US 9,002,429 B2
(45) Date of Patent: Apr. 7, 2015

(54) DIGITAL DRUG DELIVERY

(75) Inventor: Leonardo W. Estevez, Rowlett, TX (US)

(73) Assignee: Texas Instruments Incorporated, Dallas, TX (US)

( * ) Notice: Subject to any disclaimer, the term of this patent is extended or adjusted under 35 U.S.C. 154(b) by 1158 days.

(21) Appl. No.: 12/582,874

(22) Filed: Oct. 21, 2009

(65) Prior Publication Data

US 2011/0092805 A1   Apr. 21, 2011

(51) Int. Cl.
| | |
|---|---|
| *A61B 5/05* | (2006.01) |
| *A61B 5/055* | (2006.01) |
| *A61B 5/00* | (2006.01) |
| A61B 5/026 | (2006.01) |
| A61M 5/178 | (2006.01) |
| A61M 21/00 | (2006.01) |

(52) U.S. Cl.
CPC ............ *A61B 5/055* (2013.01); *A61B 5/0263* (2013.01); *A61B 5/4076* (2013.01); *A61B 5/4839* (2013.01); *A61M 5/178* (2013.01); *A61M 2021/0044* (2013.01); *A61M 2210/0693* (2013.01)

(58) Field of Classification Search
USPC ........................................ 600/407, 410–423
See application file for complete search history.

(56) References Cited

U.S. PATENT DOCUMENTS

| | | | |
|---|---|---|---|
| 7,567,693 B2 | 7/2009 | deCharms | |
| 8,082,015 B2 * | 12/2011 | Yodh et al. ..................... 600/310 |
| 2005/0273017 A1 * | 12/2005 | Gordon .......................... 600/544 |
| 2009/0318794 A1 | 12/2009 | deCharms | |
| 2010/0069739 A1 | 3/2010 | deCharms | |
| 2012/0021394 A1 | 1/2012 | deCharms | |
| 2013/0275894 A1 | 10/2013 | Bell et al. | |

FOREIGN PATENT DOCUMENTS

| | | |
|---|---|---|
| WO | WO 2013096341 | 6/2013 |
| WO | WO 2014078593 | 5/2014 |

* cited by examiner

*Primary Examiner* — Unsu Jung
*Assistant Examiner* — Joel Lamprecht
(74) *Attorney, Agent, or Firm* — Alan A. R. Cooper; Frank D. Cimino

(57) ABSTRACT

For delivery of a chemical to a target region of a subject's brain, an apparatus comprising a storage medium on which is stored digital representations of subject-specific selective visual stimuli that, when viewed, selectively stimulate blood flow to the target area of the brain; and an electronic display device coupled thereto and configured for converting the stored digital representations to images viewable by the subject; wherein the one or more selective visual stimuli were determined by exposing the subject to a plurality of potential stimuli; measuring the blood flow response to multiple regions of the brain, including the target area and one or more non-target areas; comparing the blood flow responses to the potential stimuli, and selecting as selective stimuli potential stimuli that result in relatively more blood flow to the target area and relatively less blood flow one or more non-target areas.

21 Claims, 2 Drawing Sheets

DIGITAL DRUG DELIVERY

BACKGROUND

1. Technical Field

The present invention relates generally to apparatus and methods for treating the brain. More specifically, the invention relates to apparatus and methods for treating brain tumors, selectively erasing or promoting memories, and treating addictions. Still more specifically, the present invention relates to treating the brain by chemical treatment in combination with selective stimulation of neurons in a target region or regions of the brain whereby blood flow, and thus chemical delivery, to the target region or regions is enhanced.

2. Background of the Invention

Many therapies and/or treatments directed to the brain involve the use of non-selective chemicals. Such non-selective chemicals desirably affect target region(s) of the brain, but may also undesirably affect non-target regions of the brain. For example, chemotherapy drugs may be utilized in an attempt to reduce the size and/or growth of brain tumors. When administered, for example via ingestion of a pill form of the drug or injection directly into the blood stream of the subject, such chemotherapy drugs often non-selectively attack cells in the brain, including, in addition to cancerous cells, non-cancerous cells whose destruction is undesired and produces negative effects in the patient. More selective targeting of tumor cells that minimizes negative side effects produced by undesired drug delivery to non-tumorous cells is continuously sought in the field of oncology. Such targeting generally focuses on modifying the chemotherapy drug itself to only target cancer cells, i.e. modifying the chemotherapy drug or developing new chemotherapy drugs which target rapidly growing cells.

Treatment for addiction generally comprises twelve step programs that help addicts deal with underlying issues causing their addiction. Addictions may be promoted by the dopamine reward system in the brain. Dopamine is released from an area of the brain known as the substantia nigra to the nucleus accumbens. The brain thus rewards the body for things such as activities which provide pleasure, e.g. eating and drinking, and for remembering things related to these activities. With addiction, the dopamine reward system proceeds to reward, not only the addictive activity itself, but dopamine release, and thus reward, may be triggered by various addiction cues. Cue reactivity to addictive stimuli is frequently observed in addiction, for example in drug addiction. Cue reactivity refers to a classical conditioned response pattern that results from exposure of an addict to various addiction-related stimuli. Such addiction cues, or triggers, may be, for example, ads for foods, pictures of or an actual cigarette box, drug paraphernalia such as syringes, or even thoughts of such things. In the case of such addiction, the addiction cues themselves may trigger the dopamine reward system, leading to a need for more and more of the addictive behavior to provide a desired response in the addict. Treatment for addiction sometimes thus comprises cue exposure treatment or CET, which refers to a manualized, repeated exposure to drug-related cues. Such therapy is directed to reduction of cue reactivity by extinction. Such therapy is used in an attempt to desensitize an addict from such cues, for example, by exposing them to the cues without having the addict succumb to the signals and partake in the addictive activity, e.g. smoking, drinking, eating, having sex, etc. In CET, different stimuli are presented in nonrealistic, experimental settings. Such stimuli may be presented, for example, via slides, video tapes, pictures, or paraphernalia.

Many individuals have unwanted memories they would like to forget. For example, persons surviving traumatic experiences may develop post traumatic stress disorder, or PTSD. PTSD is one of the most debilitating psychopathological conditions affecting military veterans. In PTSD, the cortisol response of the person, which generally, as a safety mechanism, serves to block such memories from memory, was inappropriate or insufficient to erase the memory of the traumatic event, and the victim thus suffers undesirable and often debilitating memories, which may materialize in lifelike form. Such memories often negatively inhibit the normal functioning of such PTSD sufferers. Treatment for PTSD sometimes involves attempting to desensitize the sufferer to the memory by imaginal exposure treatment. Such imaginal exposure may be virtual reality exposure (VRE) therapy, which is distinguished from typical imaginal exposure by a sense of presence provided by virtual reality. Such imaginal therapy is aimed at facilitating emotional processing of the undesired memories by activating the fear structure via confrontation with the stimuli, which elicits the fearful response, and modifying it. The stimuli may be visual, audio, or a combination thereof. Habituation and extinction processes lead to cessation of the anxiety response to the fear structure. The idea is that forcing the PTSD sufferer to virtually or imaginally re-experience the feared event in a controlled manner thus may lead to habituation of the patient to and extinction of the memory. Such treatment generally requires numerous therapy sessions over a substantial time period. For example, therapy may comprise 10-20 or more individual sessions of 60-90 minutes or more, twice weekly for a time period of more than 5 weeks.

Other individuals would like to enhance memory of certain things. For example, persons, generally the elderly, experiencing undesirable memory loss due to, for example, dementia or Alzheimer's, are generally treated with prescriptions for various drugs. Such people may benefit from treatments effective for enhancing the recall of various important pieces of information, such as medicine needed to be taken, healthcare providers, family members, telephone numbers, addresses, and the like.

Accordingly, there is a need for improved methods and apparatus for treating the brain for brain tumors, addictions, and erasure or enhancement of specific memories.

SUMMARY

Herein disclosed is an apparatus for targeting delivery of a treatment chemical to a target region of the brain of a subject, the apparatus comprising a storage medium on which is stored digital representations of one or more subject-specific selective visual stimuli that selectively stimulate blood flow to the target area of the brain when viewed by the subject; and an electronic display device coupled to the storage medium and configured for converting the stored digital representations to images viewable by the eye of the subject; wherein the one or more selective visual stimuli were determined by exposing the subject to a plurality of potential stimuli; measuring, for each potential stimulus, the blood flow response to multiple regions of the brain of the subject, including the target area and one or more non-target areas; comparing the blood flow responses of the potential stimuli, and selecting as selective stimuli one or more of the potential stimuli that result in relatively more blood flow to the target area and relatively less blood flow to at least one of the one or more non-target areas when the subject is exposed thereto. In embodiments, the electronic display device comprises a virtual reality system, an AR/VR system, a computer, or any combination thereof. In embodiments, measuring the blood flow response to multiple regions of the brain comprises magnetic resonance imaging. Measuring the blood flow response to multiple regions of the brain may comprise functional magnetic resonance imaging, fMRI.

In embodiments, the apparatus is further configured for presenting to the eye of the subject one or more attenuation stimuli that selectively stimulate at least one of the one or more non-target areas without substantially stimulating the target area when the subject is exposed thereto. The one or more attenuation stimuli may be determined by: (a) exposing the subject to a potential stimulus; (b) determining the response of the subject to the potential stimulus, wherein determining the response comprises determining the blood flow to the at least one target area and the one or more non-target areas in response to the potential stimulus; (c) repeating (a) and (b) for a plurality of potential stimuli; and (d) comparing the responses of the subject to the potential stimuli and selecting as at least one attenuation stimulus one or more of the potential stimuli to which the response determined in (b) was substantial blood flow to at least one of the one or more non-target areas and minimal blood flow to the at least one target area. The apparatus may be configured for exposing to the eye of the subject the one or more selective visual stimuli prior to exposing to the eye of the subject the one or more attenuation stimuli.

In embodiments, the treatment chemical stimulates blood flow to one or more non-target areas of the brain in addition to stimulating blood flow to the at least one target area and the apparatus further comprises a means for delivering an attenuation agent to the subject, wherein the attenuation agent is a chemical effective to degrade, inhibit, or otherwise minimize the effect of the treatment chemical.

In embodiments, the storage medium, the device, or both are portable by the subject. In embodiments, the apparatus further comprises a means of administering a treatment chemical to the blood of the subject. In embodiments, the means for administering a treatment chemical to the blood of the subject is selected from pills for ingestion by the subject and syringes for injection of the treatment chemical directly into the blood stream of the subject.

In embodiments, the target area of the brain of the subject comprises cancerous cells. In such embodiments, the treatment chemical may be selected from chemotherapy drugs.

In embodiments, the at least one selective stimulus comprises one or more addiction cues and the treatment chemical is selected from the group consisting of dopamine antagonists, stress hormones, and combinations thereof.

In embodiments, the apparatus is designed for effecting erasure of one or more undesired memories, the at least one selective stimulus comprises one or more images the subject relates with the one or more undesired memories and the treatment chemical is selected from glucocorticoids. In such embodiments, the treatment chemical may comprise cortisol. Such apparatus may be operable for use with a subject suffering from PTSD.

In embodiments, the apparatus is operable for effecting enhanced memory of desired information by the subject, the at least one selective stimulus comprises one or more images of the desired information and the treatment chemical is selected from amphetamines, BDNF and combinations thereof. Such apparatus may be operable for use with a subject suffering from dementia, Alzheimer's, or both.

Also disclosed is a method of providing a device suitable for use in the treatment of a brain tumor located in a target area of a brain of a subject, the method comprising: determining one or more selective visual stimuli that, when viewed by the subject, selectively stimulate blood flow to the target area of the brain by: exposing the subject to a plurality of potential stimuli; measuring, for each potential stimulus, the blood flow response to multiple regions of the brain of the subject, including the target area and a plurality of non-target areas, upon viewing the potential stimulus; comparing the blood flow response to the exposure to each of the potential stimuli and selecting as the one or more selective visual stimuli one or more of the potential stimuli to which exposure results in relatively more blood flow to the target area while resulting in relatively less blood flow to one or more of the non-target areas; and configuring a device to present to the eye of the subject the one or more selective visual stimuli. In embodiments, measuring the blood flow response to multiple regions of the brain comprises magnetic resonance imaging.

In embodiments, viewing of the one or more selective visual stimuli also stimulates blood flow to one or more undesired areas selected from the one or more non-target areas, and the method further comprises selecting as one or more visual attenuation stimuli one or more of the potential stimuli that result in relatively more blood flow to at least one of the one or more undesired areas while resulting in relatively less blood flow to the target area; and the device is further configured to present to the eye of the subject the one or more visual attenuation stimuli.

Also disclosed is a method of selectively delivering a chemical to at least one target area of a brain of a subject, the method comprising: determining at least one selective stimulus effective for selectively increasing blood flow to the at least one target area when the subject is exposed thereto; administering a treatment chemical to the blood of the subject; and exposing the subject to the at least one selective stimulus, whereby delivery of the treatment chemical to the at least one target area of the brain is enhanced via the increased blood flow stimulated by exposure of the subject to the at least one selective stimulus. In embodiments, determining at least one selective stimulus further comprises: (a) exposing the subject to a potential stimulus; (b) determining the response of the subject to the potential stimulus, wherein determining the response comprises determining the blood flow to the at least one target area in response to the potential stimulus; (c) repeating (a) and (b) for a plurality of potential stimuli; and (d) comparing the responses of the subject to the potential stimuli and providing as at least one selective stimulus one or more of the potential stimuli to which the response determined in (b) was increased blood flow to the at least one target area.

BRIEF DESCRIPTION OF THE DRAWINGS

For a more detailed description of the preferred embodiment of the present invention, reference will now be made to the accompanying drawings, wherein.

NOTATION AND NOMENCLATURE

Figure 1:
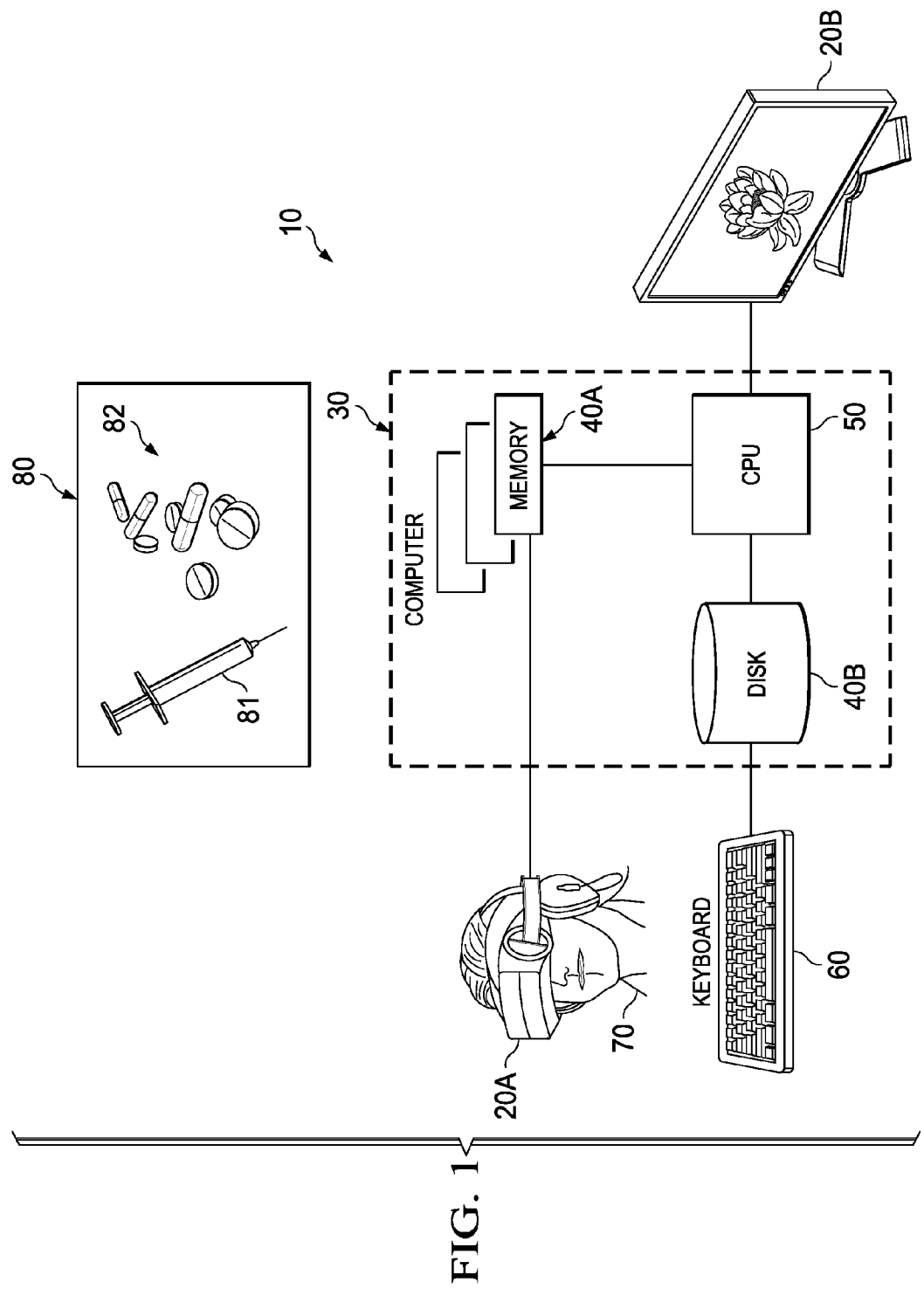
FIG. 1 is a schematic of an apparatus for digital drug delivery according to an embodiment of this disclosure.

Certain terms are used throughout the following description and claims to refer to particular system components. As one skilled in the art will appreciate, various companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ."

DETAILED DESCRIPTION

I. Overview. In various therapies and treatment programs, it is desirable to deliver non-selective drugs to specific brain regions during a periodic dosage while minimizing undesired side effects. As further discussed hereinbelow, a device effective to elicit blood flow to a combination of specific neural pathways, thus focusing a drug's absorption on a desired set of neurons, may be utilized to provide selective drug delivery. In embodiments, the therapy or treatment is staged to first treat an area of interest with effective dosing of a treatment chemical and subsequently provide attenuation stimuli and/or an attenuation agent (e.g. a degradative enzyme) that will counter the effects of the treatment chemical on unwanted central areas of the brain (for example, the occipital cortex).

As further discussed hereinbelow, the disclosed system and method may be utilized to focus the delivery of drugs within a dosage period before the drug is metabolized by the body with synchronous exposure to digital media which have been experimentally determined (for example, via fMRI) to activate a set of neural pathways which are targeted to be effected by the drug.

As discussed further hereinbelow, the disclosed system and method may enable selective delivery of a drug with high specificity to target areas of the brain with minimal side effects. If the drug is a corticosteroid, repeated exposures may cause degeneration/desensitization of the target area to the stimuli. If the drug is intended to treat a tumor or enhance activity of a degenerate area, repeated exposures to combinations of neural circuits with the area of the tumor or degenerate neurons in common may minimize collateral damage typically associated with chemotherapy or excitotoxicity. That is, directing specific drugs to specific areas via the disclosed system and method may provide a differentiated effect as opposed to administration of such drugs in the absence of exposure of a subject to an accompanying stimulus pattern, in which case the drugs may be directed to substantially all or a greater number of regions of the brain.

Without wishing to be limiting, the drug or drugs administered via the disclosed system and method may be selected from, for example: agonists, which are drugs that act as endogenous chemicals on cell receptors; antagonists, which are drugs that block an endogenous chemical from activating cell receptors; and reuptake inhibitors, which are drugs which prevent endogenous chemicals from being quickly reabsorbed into cells after release, thus increasing their activation of cell receptors.

II. Apparatus for Digital Drug Delivery. Herein disclosed is an apparatus for digital drug delivery. FIG. 1 is a schematic of an apparatus 10 for digital drug delivery according to an embodiment of this disclosure. The apparatus is configured for stimulating blood flow to a desired region or regions of a brain of a subject 70 via exposure of the subject one or more selective stimulus. The digital drug delivery apparatus comprises a storage medium on which is stored digital representations of one or more subject-specific selective visual stimuli that selectively stimulate blood flow to the target area of the brain; along with an electronic display device coupled to the storage medium and configured for converting the stored digital representations to images viewable by the eye of the subject. Suitable storage media include semiconductor memory, magnetic storage and optical storage. As indicated in the embodiment of FIG. 1, the storage medium of apparatus 10 may comprise a memory 40A of a computer 30, a disk 40B of a computer 30, or both. As further discussed hereinbelow, the electronic display device of apparatus 10 may comprise, as indicated in the embodiment of FIG. 1, a virtual reality headgear 20A, a computer monitor 20B, or both. Other suitable electronic display devices include slide projectors, movie projectors, digital books, etc. The apparatus 10 and/or the medium therein may be a mobile or portable device, easily transported from location to location by a subject. In embodiments wherein the storage medium is part of a computer 30, a keyboard 60 may be attached thereto for initiating/terminating exposure of the subject 70 to images, a CPU as known in the art, and a display 20B.

In embodiments, the digital drug delivery apparatus is suitable for use in the treatment of a brain tumor located in a target area of a brain of a subject. In such embodiments, the digital drug delivery apparatus comprises storage medium on which is stored digital representations of one or more subject-specific selective visual stimuli that selectively stimulate blood flow to the target area of the brain in which the tumor is located when viewed by the subject; and an electronic display device configured for converting the stored digital representations to images viewable by the eye of the subject; wherein the one or more selective visual stimuli are determined by exposing the subject to a plurality of potential stimuli; measuring, for each potential stimulus, the blood flow response to multiple regions of the brain of the subject, including the target area and one or more non-target areas; comparing the blood flow responses to the potential stimuli, and selecting as selective stimuli one or more of the potential stimuli that result in relatively more blood flow to the target area and relatively less blood flow to at least one of the one or more non-target areas when the subject is exposed thereto. The apparatus, the storage medium, or both are portable by the subject, in some embodiments.

As discussed further hereinbelow, the apparatus may be further configured for presenting to the eye of the subject one or more attenuation stimuli that selectively stimulate at least one of the one or more non-target areas without substantially stimulating the target area when the subject is exposed thereto. In embodiments, the apparatus is configured for providing to the eye of the subject the one or more subject-specific selective visual stimuli prior to providing to the eye of the subject the one or more attenuation stimuli.

Figure 3:
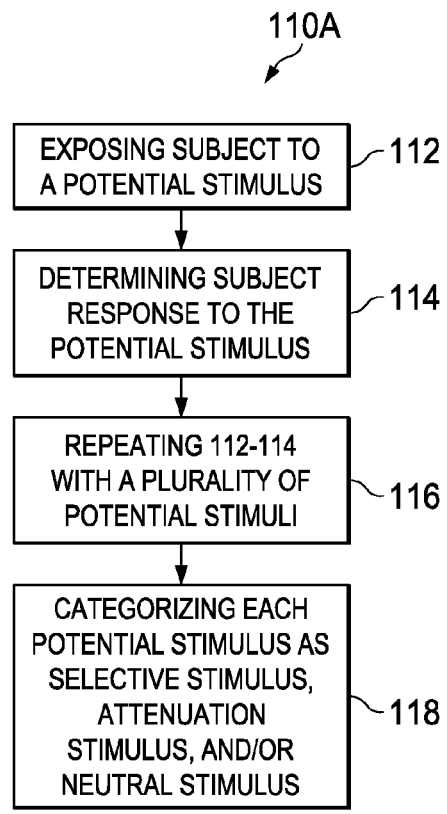
FIG. 3 is a block flow diagram of a method of providing one or more selective stimulus and/or attenuation stimulus according to an embodiment of this disclosure.

As indicated in FIG. 3, discussed further hereinbelow, the one or more selective stimulus may be determined by exposing a subject to a potential stimulus 112, determining a response of the subject to the potential stimulus 114, repeating steps 112 and 114 with a plurality of potential stimuli at 116, and categorizing each potential stimulus as selective stimulus, attenuation stimulus, and/or neutral stimulus at 118. Each of these steps is discussed further in Section III hereinbelow. As discussed in more detail below, determining a response of the subject to the potential stimuli may comprise measuring the blood flow response to multiple regions of the brain. Blood flow response may be measured utilizing magnetic resonance imaging. The blood flow response may be measured utilizing functional magnetic resonance imaging, fMRI.

The one or more selective stimuli may be visual, auditory, tactile, olfactory, gustatory, or a combination thereof. In embodiments, at least one of the one or more selective stimuli is selected from visual stimuli. In embodiments, the one or more selective stimuli comprise images. Suitable visual stimuli include, but are not limited to, still images, augmented reality environments, virtual reality environments, and combinations thereof. In embodiments, the device comprises a plurality of still images. In embodiments, the device comprises an augmented reality and/or virtual reality apparatus configured to provide one or more selective visual stimulus capable of being viewed with the human eye. The selective visual stimuli may comprise, for example, images related to undesirable memories (e.g. war images, car crashes, rape) or images associated with an addiction (e.g. images of drugs and/or drug paraphernalia, images of various foods).

In embodiments, the one or more selective stimulus comprises a selective auditory stimulus. For example, auditory stimuli may comprise addiction cues, such as audio of commercials for addictive substances including, but not limited to, cigarettes and foods, the sound of beverages being opened and/or poured, sounds associated with undesirable memories (e.g. the sound of a car crash), or any combination thereof.

In embodiments, the one or more selective stimuli comprise a selective olfactory stimulus. For example, olfactory stimuli may comprise smells associated with undesirable memories such as, but not limited to, the smell of fire/smoke, burnt rubber) or smells associated with addictive substances, such as, but not limited to, cigarettes, cigars, marijuana, In embodiments, the one or more selective stimulus comprises tactile stimulus. Such stimulus may comprise, but is not limited to, the feel of drugs and/or drug paraphernalia (e.g. syringe, beer bottle), the feel of items associated with undesirable memories (e.g. weapons), or a combination thereof.

In embodiments, the one or more selective stimulus comprises a gustatory stimulus. Such stimulus may comprise, but is not limited to, a food product, the taste of a cigarette/cigar or a drug in the mouth, etc.

The selective stimuli may stimulate one or more core or ancillary regions of the brain in addition to a desired region or regions. In embodiments, in addition to being configured to provide one or more selective stimulus, such selective stimuli effective for stimulating a desired region or regions of a brain of a human, the device is also configured to provide attenuation stimuli, such attenuation stimuli effective for stimulating one or more regions of the brain stimulated by the effective stimuli but not considered a desired or targeted region. Attenuation stimuli may be selected as those potential stimuli that are found to stimulate enhanced blood flow to one or more non-target regions of the brain of the subject while not stimulating or minimally stimulating the target area(s). Attenuation stimuli comprise one or more of visual, audio, olfactory, gustatory, and tactile stimuli that have been determined to stimulate said core or ancillary region(s) of the brain without substantially stimulating the desired region or regions of the brain.

In embodiments, the one or more selective stimuli may be effective for stimulating a region of the brain comprising a tumor. In embodiments, the one or more selective stimulus is effective for stimulating a reward center of the brain. In embodiments, the selective stimulus is effective at stimulating blood flow to a memory center of the brain. In embodiments, the one or more attenuation stimulus is effective for stimulating one or more core region of the brain. In embodiments, the one or more core region is selected from the occipital cortex, Brodmann's area 6, the hippocampus, and hypothalamic regions.

In embodiments, the one or more selective stimuli are effective for stimulating region(s) of the brain associated with unwanted memories. Such stimuli may, in embodiments, be provided by a subject. In embodiments, the one or more selective stimulus is information a subject would like to selectively remember, such as important personal information, including medical requirements/drug dosages, home address, telephone number(s), family or caregiver relationship to the subject, names, telephone numbers, addresses, and the like.

In embodiments, the one or more selective stimulus is effective at stimulating blood flow to region(s) of the brain associated with addiction triggers. Such stimuli may be obvious based on the addiction, or may be provided by the subject.

The drug delivery apparatus may be configured to present visual stimuli as slide projections, as pictures on paper, a computer display, an augmented reality environment, a virtual reality environment, or a combination thereof. In embodiments, the apparatus comprises a storage medium on which is stored digital representations of one or more subject-specific selective visual stimuli and an electronic display device configured for converting the stored digital representations to images viewable by the eye of the subject. As mentioned hereinabove, the storage medium may be any storage medium known in the art, including, but not limited to, semiconductor memory, magnetic storage and optical storage. The electronic display device can be selected from virtual reality systems 20A, AR/VR systems, computer monitors 20B, and combinations thereof. The apparatus may comprise an augmented reality/virtual reality or AR/VR system, as known in the art. For example, the apparatus may comprise a head-mounted display 20A. The apparatus may further comprise a tracking system, headphones, and/or an interaction device. In embodiments, a head mounted display is used in conjunction with a head tracker, as known in the art. Suitable head trackers include, but are not limited to, InterTrax II or InsideTrak position tracker, available from Polhemus. Programming may be done as known in the art, for example, via True Space TCL, Lightning (virtual interaction and animation software package, available from Stuttgart, Germany, or a combination thereof. The virtual environment may be visualized as known in the art, for example via a Silicon Graphics (SGI) Onyx Deskside System for data processing.

In embodiments, the apparatus 10 for digital drug delivery comprises a device configured for stimulating a desired region or regions of a brain of a human with one or more selective stimulus as described above and one or more means 80 for administering a chemical to the bloodstream of a patient. The means for administering a chemical to the bloodstream of a patient 80 may comprise any means known in the art for supplying a chemical to the bloodstream of a patient. Such means include, but are not limited to, ingestible chemicals (e.g. pills 82) whereby a chemical is digested and absorbed into the bloodstream, injection means for introducing a chemical directly to the bloodstream (e.g. a syringe 81, and/or IV apparatus), and combinations thereof. Utilization of pills may be more convenient for self-administering of the treatment chemical and/or attenuation chemical by a subject, but will generally require longer sessions, as time for metabolism of the pill and incorporation into the bloodstream must be taken into account. Injection of the chemical and/or attenuation agent may provide for more rapid treatment sessions, requiring less time between injection (administering of treatment chemical or attenuation agent, respectively) and exposure to the one or more stimulus (selective or attenuation, respectively).

Figure 2:
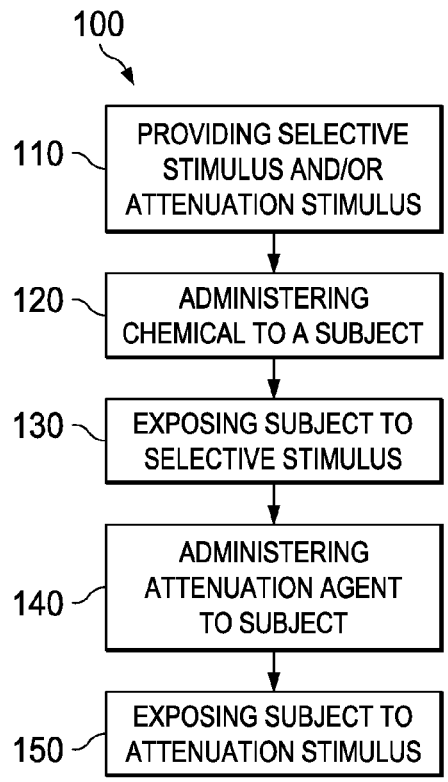
FIG. 2 is a block flow diagram of a method of digital drug delivery according to an embodiment of this disclosure.

III. Method of Digital Drug Delivery. Herein disclosed is a method of digital drug delivery. FIG. 2 is a block flow diagram of a digital drug delivery (DDD) method 100 according to an embodiment of this disclosure. Digital drug delivery method 100 comprises providing a selective stimulus and/or attenuation stimulus 110, administering a chemical to a subject 120, and exposing the subject to selective stimulus 130. Digital drug delivery method 100 may further comprise administering attenuation agent 140 and/or exposing the subject to attenuation stimulus 150.

Digital drug delivery method 100 comprises providing selective stimulus and/or attenuation stimulus. Providing selective stimulus and/or attenuation stimulus 110 comprises providing one or more selective stimulus that is effective for stimulating blood flow to a desired region or regions of a brain. In embodiments, providing selective stimulus and/or attenuation stimulus 110 further comprises providing one or more attenuation stimulus effective for stimulating one or more regions of the brain to which blood flow is stimulated by the selective stimulus but which is not considered a desired region(s). One or more selective stimulus may be provided by combining one or more known selective stimulus. For example, in the treatment of addiction, one or more known addiction cues may be combined and provided as selective stimuli. By way of another example, in selective memory erasure, providing one or more selective stimulus may comprise providing one or more stimulus known to trigger undesired memories in a subject which the subject would like to forget.

According to an embodiment of this disclosure, providing selective stimulus and/or attenuation stimulus may comprise a calibration phase in which one or more selective stimulus and/or attenuation stimulus are determined. FIG. 3 is a block flow diagram of a method of calibration 110A. Calibration method 110A may be utilized to determine one or more selective stimulus, one or more attenuation stimulus, or both. Method 110A comprises exposing a subject to a potential stimulus at 112, determining a response of the subject to exposure to the potential stimulus at 114, repeating steps 112 and 114 with a plurality of potential stimuli at step 116, and categorizing each potential stimulus as a selective stimulus, an attenuation stimulus, or a neutral stimulus at 118. Method 110A may be utilized to provide selective and/or attenuation stimuli for use in a method of treating a brain tumor, for example, as further discussed hereinbelow.

Exposing a subject to a potential stimulus 112 comprises having a subject view a potential visual stimulus (i.e. an image), smell a potential olfactory stimulus (i.e. an odor), touch a potential tactile stimulus (i.e., an object), taste a potential gustatory stimulus (e.g. a food) or listen to a potential auditory stimulus (i.e. a sound, e.g. the sound of a helicopter, a song, a taped statement). The potential stimulus may be in any of the categories discussed above for selective and attenuation stimuli.

Various equipment suitable for exposing a subject to a potential stimulus is known in the art. For example, exposing the subject to a potential stimulus may comprise having the subject view an image on a slide, an image on a page, an image on a screen, or the like. Utilization of AR/VR apparatus to expose the subject to a 3D projection of the potential stimulus (and to the one or more selective stimuli at 130 and the one or more attenuation stimuli at 150, where utilized) may be more effective than 2D representations of the images, as such exposure more closely approaches reality. Various AR/VR apparatus are known in the art. Any such apparatus may be utilized to expose a subject to a potential stimulus at 112. For example, exposing a subject to a potential stimulus may comprise having the subject view a slide, a picture on a page, an image on a computer screen, or an image presented to the subject via augmented and/or virtual reality. Exposing a subject to a potential stimulus may comprise having the subject eat a potential gustatory stimulus. For example, the subject may consume a food to which the subject is addicted or place in his mouth an item to which he is addicted, e.g. a drug such as a cigarette or cigar. Exposing the subject to a potential stimulus may comprise having the subject listen to a potential auditory stimulus. Such potential auditory stimulus can be the sound of an object the subject relates with a memory the subject desires to selectively erase, for example, a portion of a song that brings to the subject an unwanted memory, a sound related to war, a sound of anger, a tape of the voice of one or more person the subject would like to forget, or any other sound which conjures memories the subject would like to selectively erase. Such potential auditory stimulus can be a sound that acts as an addiction cue for the subject. Such a potential auditory stimulus can be, for example, an ad for a particular food or snack, an ad for cigarettes/cigars, the sound of a can of beer opening, and the like. Exposing a subject to a potential stimulus may comprise having the subject touch a potential tactile stimulus. Such a potential tactile stimulus may be an addiction cue, such as a cigarette or cigar, drug paraphernalia such as a syringe, a food addiction cue such as a dessert, and the like. Such a potential tactile stimulus may be an object that, when touched, is related in the subject's brain with an unwanted memory. Such an object can comprise, for example, a weapon and etc. Exposing a subject to a potential stimulus may comprise having the subject smell a potential olfactory stimulus. Such a potential olfactory stimulus may be an addiction cue, such as the smell of a cigarette or cigar or other drug, the smell of a food such as fresh-baked cookies, and the like. Such a potential olfactory stimulus may be a smell that is related in the subject's brain with an unwanted memory. Such a potential olfactory stimulus can comprise, for example, the smell of smoke/fire, gunpowder, and the like.

Calibration method 110A further comprises determining the response of the subject to the potential stimulus at 114. Determining the response of the subject to the potential stimulus comprises measuring the blood flow to various regions of the brain following exposure of the subject to the potential stimulus. The blood flow to various regions of the brain may be determined by any means known in the art. For example, blood flow in the brain may be determined using PET, CT, MRI, or a combination thereof. In embodiments, blood flow to various regions of the brain is determined using functional Magnetic Resonance Imaging or fMRI. The fMRI may be BOLD fMRI, diffusion based functional MRI, contrast MR, arterial spin labeling, magnetic resonance spectroscopic imaging, diffusion tensor imaging, or a combination thereof.

Steps 112 and 114 are repeated with a plurality of potential stimuli at step 116. The plurality of potential stimuli may be selected randomly. The plurality of potential stimuli may comprise orthogonal concepts. Different subjects will respond differently to various stimuli, for example, based on past history, hobbies and interests, and etc. Thus, a variety of stimuli may be tested for each subject and the selective stimuli suitable for a specific subject determined via the calibration phase comprising calibration method 110A. The potential stimuli may be selected based on the interests, hobbies, life history of the subject. Such potential stimuli may comprise, for example, images of alphanumeric characters, animals, objects relevant to a subject's hobbies and/or interests, addiction cues, cues to undesired memories, desired memories, or some combination thereof.

Method 110A further comprises categorizing each potential stimulus as selective stimulus, attenuation stimulus, or neutral stimulus at 118 based on the subject response in 114. For example, if a tumor is known to be in an area A and the potential stimulus effects blood flow into area A, the potential stimulus may be categorized as a selective stimulus, depending on the extent of other brain regions stimulated. A suitable selective stimulus may enhance blood flow to area A while minimizing blood flow to areas of the brain outside area A.

Providing selective stimulus and/or attenuation stimulus at 110 may further comprise providing attenuation stimulus. One or more attenuation stimulus may be selected subsequent determination of the one or more selective stimulus. The one or more attenuation stimulus may stimulate and thus increase blood flow to one or more areas of the brain outside the desired or target region (i.e., outside the region to which increased blood flow and selective drug delivery is desired). For example, exposure to selective stimuli may effect stimulation of core regions of the brain, such as the occipital cortex, Brodman's area 6, the hippocampus, and/or thalamic regions, in addition to effecting stimulation of blood flow to a desired region(s) of the brain. For example, the one or more selective stimulus may stimulate desired region(s) A of a brain and also stimulate blood flow to undesired region(s) B of the brain. One or more attenuation stimulus may be selected by repeating steps 112, 114 as at step 116 with various potential stimulus until one or more potential stimulus is found to stimulates region(s) B of the brain without substantially stimulating region(s) A. Such a stimulus will be categorized at 118 as a suitable attenuation stimulus.

Stimuli which are neither selective nor attenuation stimuli are categorized as neutral stimuli and are rejected for use in the disclosed method and apparatus. In embodiments in which attenuation stimuli are not utilized/incorporated, attenuation stimuli are categorized as neutral stimuli and rejected for use in the disclosed apparatus and method.

Referring again now to FIG. 2, digital drug delivery method 100 further comprises administering a chemical to a subject at 120. Administering a chemical to the subject can comprise having the subject ingest a pill or injecting a chemical into the bloodstream of the subject. In embodiments, the method is utilized to treat a brain tumor and the chemical comprises a chemotherapy drug as known in the art. In embodiments, the chemotherapeutic drug is selected from alkylating agents, antimetabolites, anthracyclines, plant alkaloids, topoisomerase inhibitors, other antitumor agents, and combinations thereof. In embodiments, the chemical is a drug that affects cell division or DNA synthesis and function. In embodiments, the chemical does not directly interfere with DNA. In embodiments, the chemical is selected from monoclonal antibodies and tyrosine kinase inhibitors.

In the following, Anatomical Therapeutic Chemical Classification System codes are provided. In embodiments, the chemical comprises a chemotherapy drug. In embodiments, the chemotherapy drug is selected from known alkylating agents (L01A). The chemical may comprise an alkylating antineoplastic agent. In embodiments, the alkylating agent is selected from cisplatin, carboplatin, and oxaliplatin. In embodiments, the chemical is selected from mechlorethamine, cyclophosphamide, chlorambucil, ifosfamide that work by chemically modifying the DNA of a cell. In embodiments, the chemotherapy drug is selected from anti-metabolites (L01B), currently the most widely used cytostatics. Anti-metabolites masquerade as purine (azathioprine, mercaptopurine) or pyrimidine, which become the building blocks of DNA. Anti-metabolites prevent such substances from becoming incorporated in DNA during the "S" phase (of the cell cycle), stopping normal development and division and also affect RNA synthesis. In embodiments, the chemotherapy drug is selected from plant alkaloids and terpenoids (L01C). Such alkaloids are derived from plants and block cell division by preventing microtubule function. Without these microtubules, cell division cannot occur. In embodiments, the chemical is selected from vinca alkaloids and taxanes. In embodiments, the chemical is selected from vinca alkaloids (L01CA). Vinca alkaloids bind to specific sites on tubulin, inhibiting the assembly of tubulin into microtubules (M phase of the cell cycle). In embodiments, the vinca alkaloid is derived from the Madagascar periwinkle, *Catharanthus roseus* (formerly known as *Vinca rosea*). In embodiments, the chemical is selected from the following vinca alkaloids: vincristine, vinblastine, vinorelbine, and vindesine. In embodiments, the chemical is a podophyllotoxin (L01CB). Podophyllotoxin is a plant-derived compound which is said to help with digestion as well as used to produce two other cytostatic drugs, etoposide and teniposide. In embodiments, the chemical is derived from the American Mayapple (*Podophyllum peltatum*) or the Himalayan Mayapple (*Podophyllum hexandrum*). The chemical may be derived recombinantively. In embodiments, the chemotherapy drug is selected from taxanes (L01CD). In embodiments, the taxane is the natural product paclitaxel, originally known as Taxol and first derived from the bark of the Pacific Yew tree. In embodiments, the chemotherapy drug comprises docetaxel, which is a semi-synthetic analogue of paclitaxel. Taxanes enhance stability of microtubules, preventing the separation of chromosomes during anaphase. In embodiments, the chemotherapy drug is selected from topoisomerase inhibitors (L01CB and L01XX) Topoisomerases are essential enzymes that maintain the topology of DNA. Inhibition of type I or type II topoisomerases interferes with both transcription and replication of DNA by upsetting proper DNA supercoiling. In embodiments, the chemotherapy drug is selected from type I topoisomerase inhibitors. In embodiments, the type I topoisomerise inhibitor is selected from camptothecins: irinotecan and topotecan. In embodiments, the chemotherapy drug is selected from type II topoisomerase inhibitors. In embodiments, the type II topoisomerase inhibitor is selected from amsacrine, etoposide, etoposide phosphate, teniposide, and combinations thereof. These drugs may be semi-synthetic derivatives of epipodophyllotoxins, alkaloids naturally occurring in the root of American Mayapple (*Podophyllum peltatum*). In embodiments, the chemotherapy drug is selected from antitumor antibiotics (L01D), including, but not limited to, the immunosuppressant dactinomycin (which is used in kidney transplantations), doxorubicin, epirubicin, bleomycin and others. Administering the chemotherapy drug to a subject 120 along with exposing the subject to selective stimulus 130 will enhance the delivery of the drug to a target area(s) of the brain, as discussed further below.

In embodiments, digital drug delivery method 100 is utilized for selective memory erasure. Such selective memory erasure may be desirable to a subject suffering from post traumatic stress disorder (PTSD), a subject having difficulty dealing with a past event such as divorce or the death of a child, or any subject having a memory he or she would like to selectively erase. In such embodiments, administering a chemical to the subject at 120 may comprise administering cortisol to the subject. Cortisol is a corticosteroid hormone or glucocorticoid produced by the adrenal cortex which is part of the adrenal gland. Cortisol is involved in response to stress and anxiety, controlled by corticotrophin-releasing hormone, CRH, and large amounts of cortisol are toxic to neurons. The chemical administered at 120 may comprise any of various synthetic forms of cortisol known in the art. The chemical may comprise a natural metabolic intermediary of cortisol, such as hydrocortisone (may be referred to as Compound E). Cortisol cooperates with epinephrine (adrenaline) to create memories of short-term emotional events. As further discussed hereinbelow, administering cortisol at 120 to a subject along with exposing the subject to selective stimulus at 130 will enhance the delivery of cortisol to region(s) of the brain associated with the unwanted memories, enhancing erasure thereof by disconnecting the neural pathway associated with the unwanted memory.

In embodiments, digital drug delivery method 100 is utilized for selective memory enhancement. In such embodiments, administering chemical to the subject 120 may comprise administering a chemical known to stimulate memory, such as Ritalin, brain-derived neurotrophic factor, or BDNF, and the like. In such applications, chemical administering at 120 will be combined with exposure of the subject at 130 to material he/she desires to selectively remember, such as school materials, business documents, data important to his/her life, or the like. For example, an elderly subject with onset dementia/Alzheimer's may be given a memory stimulating chemical at 120 and exposed at 130 to important personal information, such as medical requirements, home address, telephone number(s), family or caregiver relationship to the subject, names, telephone numbers, addresses, and the like. In this manner, the subject may maintain a "normal" life in spite of the onset infirmity.

In embodiments, digital drug delivery method 100 is utilized for treating an addiction. In such embodiments, administering a chemical to the subject at 120 may comprise administering a drug that inhibits dopamine. A dopamine antagonist is a drug which blocks dopamine receptors by receptor antagonism. In embodiments, the drug is a dopamine antagonist selected from the group consisting of acepromazine, amisulpride, amoxapine, azaperone, benperidol, bromopride, butaclamol, chlorpromazine, chlorprothixene, clopenthixol, clozapine, domperidone, droperidol, eticlopride, flupenthixol, fluphenazine, fluspirilene, haloperidol, loxapine, mesoridazine, levomepromazine, metoclopramide, nafadotride, nemonapride, olanzapine, penfluridol, perazine, perphenazine, pimozide, prochlorperazine, promazine, quetiapine, raclopride, remoxipride, risperidone, spiperone, spiroxatrine, stepholidine, sulpiride, sultopride, tetrahydropalmatine, thiethylperazine, thioridazine, thiothixene, tiapride, trifluoperazine, trifluperidol, triflupromazine, and ziprasidone.

In some embodiments for treating drug addiction, administering a chemical to the subject at 120 may comprise administering a drug that provides a negative response (e.g., a stress response) from the subject. Such a drug may be selected from norepinephrine and norepinephrine reuptake inhibitors. A norepinephrine reuptake inhibitor (NRI, NERI) or adrenergic reuptake inhibitor (ARI), is a type of drug which acts as a reuptake inhibitor for the neurotransmitters norepinephrine (noradrenaline) and epinephrine (adrenaline) by blocking the action of the norepinephrine transporter (NET). This blocking results in increased extracellular concentrations of norepinephrine and epinephrine and therefore an increase in adrenergic neurotransmission. In embodiments, the chemical administered is or comprises a drug selected from selective norepinephrine reuptake inhibitors (NRIs); norepinephrine-dopamine reuptake inhibitors (NDRIs); tricyclic antidepressants (TCAs) and tetracyclic antidepressants (TeCAs). NRIs include, without limitation, atomoxetine/tomoxetine; mazindol; reboxetine; viloxazine. NDRIs include, without limitation, amineptine; bupropion; dexmethylphenidate; fencamfamine; fencamine; lefetamine; pipradrol; prolintane; and pyrovalerone. SNRIs include, without limitation, desvenlafaxine; duloxetine; milnacipran; and venlafaxine. TCAs include, without limitation, amitriptyline; butriptyline; clomipramine; desipramine; dosulepin; doxepin; imipramine; lofepramine; nortriptyline; protriptyline; and trimipramine. TeCAs include, without limitation, amoxapine; maprotiline; and mianserin. In embodiments, the norepinephrine reuptake inhibitor is selected from cyclobenzaprine; mesocarb; nefazodone; nefopam; sibutramine; tapentadol; tramadol; and ziprasidone. As discussed above, administering the addiction treatment chemical to a subject at 120 along with exposing the subject to selective stimulus (i.e. addiction cues) at 130 will enhance the delivery of the chemical to region(s) of the brain associated with the cueing, thus enhancing desensitization of the subject to the addiction cue(s).

The amount of the chemical administered at 120 will be selected based on the chemical, the subject, the metabolism of the subject (for cases in which the chemical is ingested), and the results obtained via each session of treatment. The dose-response relationship (or 'exposure-response relationship') describes the change in effect on a subject caused by differing levels of exposure (or doses) to a chemical after a certain exposure time. The amount of the chemical administered at 120 may be selected based on a dose curve or dose-response relationship, as known in the art.

Digital drug delivery method 100 further comprises exposing the subject to the selective stimulus at 130. The drug delivery device of Section II herein may be utilized to expose the subject to one or more selective stimuli. Exposing the subject to selective stimulus 130 may be performed prior to, during, and/or subsequent administering chemical to the subject at 120. In embodiments, following administration of the chemical to the subject at 120, the subject is exposed at 130 to the selective stimulus provided in step 110. In embodiments, exposing the subject to selective stimulus 130 occurs at least 5 min, 10 min, 15 min, 30 min, 45 min, or one hour following administering chemical to the subject at 120. Exposure of the subject to selective stimulus at 130 may comprise exposing the subject to selective stimulus for a period of or at least 5, 10, 15, 20, 30, 40, 45, 50, 55, or 60 minutes.

Exposing the subject to the selective stimulus 130 causes neurons in desired target area(s) to fire. The firing of the neurons consumes oxygen and glucose and blood flow is increased to the area to maintain operation of the neurons. Exposing the subject to the selective stimulus at 130 thus enhances blood flow to neurons within the target area(s) of the brain. Exposing the subject to the selective stimulus will also stimulate blood flow to neurons in certain core areas of the brain. For example, visual stimuli will stimulate the parietal cortex, an association cortex. Exposing the subject to the selective stimulus or stimuli at 130 will direct a larger concentration of the chemical administered to the subject at step 120 to the target area(s) of the brain due to enhanced flow of blood to the target area(s) encouraged by exposure of the subject to the one or more selective stimulus. Exposing the subject to the selective stimulus 130 increases the efficacy with which the administered chemical is directed to the target or desired region(s) of the brain. For example, in certain brain tumor treatment applications, exposing the subject at 130 to one or more selective stimulus that has been determined to increase blood flow to the region of the brain where the tumor is located following introduction of a chemotherapy drug into the blood of the subject (via indirect ingestion or direct injection) at 120 enhances the percentage of the administered drug that reaches the target tumor. As another example, for the selective erasure of memories, exposing the subject at 130 to one or more selective stimulus which has been determined to increase blood flow to the region of the brain associated with the undesired memory(ies) following administering cortisol to the subject at 120 will enhance application of cortisol to the target region and aid in accelerating memory recharacterization. As another example, for the treatment of addiction, exposing the subject at 130 to selective stimulus (e.g., an addition cue) that increases blood flow to a certain region of the brain associated with the trigger following administering of reward-reducing drug (e.g. dopamine inhibitor) or negative effect-inducing drug (e.g. norepinephrine) to the subject at 120 will desensitize the subject to the addiction cue(s) presented as the one or more selective stimulus.

Digital drug delivery method 100 may further comprise administering attenuation agent to the subject 140 and/or exposing the subject to one or more attenuation stimulus 150. Steps 140 and/or 150 may be utilized when exposure of the subject to the one or more selective stimulus stimulates one or more region of the brain in addition to the desired region(s) of the brain and wherein the effect of the chemical to be utilized at 120 on the one or more additional regions is undesirable, e.g. where the chemical is a chemotherapy drug. The inhibitory or attenuation chemical may be, for example, an enzyme or other chemical that degrades or otherwise deactivates or reduces the effects of the chemical administered at step 120. Exposure of the subject to attenuation stimulus 150 along with administering of attenuation agent 140 may be used, in certain embodiments, to mitigate the effects of the chemical administered at step 120 on non-target areas of the brain (e.g. core areas that are activated by exposure of the subject to the one or more selective stimulus, but which are not themselves target areas), while allowing maximum exposure of target areas of the brain (i.e., while not deactivating the delivery of the chemical administered at 120 to the target regions). For example, in treatment of a brain tumor, following administering a chemotherapy agent at 120 and exposing the subject to selective stimulus at 130, the subject may be administered an inhibitory chemical at 140 and/or exposed at 150 to one or more attenuation stimulus provided at 110. The drug delivery device of Section II herein may be utilized to expose the subject to one or more attenuation stimuli.

Administering a chemical at 140 that degrades or otherwise inhibits the chemotherapy drug (herein referred to as an 'inhibiting chemical' or 'attenuation agent') while exposing the subject to one or more attenuation stimulus at 150 may serve to diminish exposure of non-targeted areas of the brain (i.e., non-tumor areas) to the chemotherapy agent. For example, the chemotherapy agent may stimulate area(s) B of a brain in addition to area(s) A containing the tumor. The administering of the one or more attenuation agent at 140 in conjunction with exposing the subject to attenuation stimulus at 150 may reduce undesirable effects of the chemotherapy drug on non-target areas of the brain (i.e., on areas B of the brain to which drug delivery is undesired). The attenuation agent may comprise, for example, an enzyme that degrades the chemotherapy drug. Digital drug delivery method 100 may comprise step 140 and not comprise step 150, may comprise step 140 prior to step 150, may comprise step 150 prior to step 140, or may comprise concomitant performance of steps 140 and 150. That is, attenuation agent may be administered at 140 in the absence of exposing the subject to attenuation stimulus 150 or attenuation agent may be administered at 140 before during and/or after exposure of the subject to attenuation stimulus at 150.

As cortisol is naturally metabolized by the body, administering of attenuation agent 140 and exposing subject to attenuation stimulus 150 may be unnecessary with selective memory erasure as described herein. However, in certain applications, excess amounts of cortisol may be administered to speed up memory erasure. In such applications, attenuation agent may be administered at 140 and/or the subject exposed to an attenuation stimulus at 150 to reduce damage to areas of the brain such as the Hippocampus. In such instances, delivery of attenuation agent administered at 140 may be directed to the same areas to which the treatment chemical administered at 120 is directed. In such instances, the same set of one or more stimulus may serve as selective and attenuation stimuli. For example, in instances wherein it is desirable to expose a central brain region (such as, for example, the Hippocampus) of a subject to a specific chemical for a specified period of time, the same stimulus pattern may be utilized for stimulation and attenuation phases. In such applications, the attenuating chemical may used to rapidly degenerate the primary treatment drug and thus accelerate treatment cycles without endangering the subject.

Administering attenuation agent 140 and/or exposing the subject to attenuation stimulus 150 may also be unnecessary in the treatment of addiction as described herein, as the chemical administered at 130 may be naturally metabolized by the body. Again, should excess amounts of chemical be administered at 130 to enhance the treatment, an attenuation agent may be administered at 140 and/or the subject exposed to an attenuation stimulus at 150 to reduce damage to areas of the brain such as the Hippocampus. For example, some mechanism of determining if treatment beyond a certain time/amount is detrimental to the subject and a mechanism to abort treatment at this point may be used to rapidly treat a subject and/or minimize concomitant detrimental affects on the subject. In chemotherapy, for example, a goal is to direct as much chemotherapy drug to a tumor as possible with as little negative affect on the subject as possible.

IV. Method of Providing Mobile Device for Digital Drug Delivery. Also disclosed herein is a method of providing a mobile device for digital drug delivery. Providing a mobile device for digital drug delivery comprises determining one or more selective visual stimuli and providing a device configured to present to the eye of the subject the one or more selective visual stimuli. The device may be configured as a portable, mobile unit for use by the subject.

One or more selective stimulus may be determined as described with respect to FIG. 3 and calibration method 110A hereinabove. That is, a subject may be exposed to a potential stimulus at 112, the subject's response to the potential stimulus determined as at 114, and the potential stimulus categorized as a selective stimulus at step 118 if it stimulates a desired region(s) of the brain without stimulating or while only minimally stimulating (relative to the response of the other potential stimuli considered) the desired areas stimulated by the selective stimulus. Steps 112 and 114 may be repeated until a suitable number of selective stimuli are determined.

Should utilization of an attenuation stimulus be desired, providing a mobile device may also comprise determining one or more attenuation stimulus and packaging the attenuation stimuli in the mobile device. One or more attenuation stimulus can be determined by determining what non-desired areas of the brain of the subject are stimulated by exposure to the one or more selective stimulus in addition to the desired area(s) and categorizing potential stimuli as attenuation stimuli at 118 if the potential stimulus stimulates such non-desired areas of the brain while not stimulating or minimally stimulating (relative to the other potential stimuli examined) the desired areas stimulated by the one or more selective stimulus.

The stimuli may be provided as images. For example, the stimuli may be provided as a flip-through booklet or a set of pictures or slides comprising the selective stimuli grouped together and, if present in the mobile device, the attenuation stimuli grouped together. Alternatively, the mobile device may comprise a computer programmed to, upon activation by the subject (e.g., by pressing a start button), display the selective stimuli sequentially, concomitantly, or semi-continuously. The computer may also be programmed to, perhaps upon additional activation by the subject (e.g., pressing a second start button), display the attenuation stimuli sequentially, concomitantly, or semi-continuously after displaying the one or more selective stimulus. Alternatively, the mobile device may comprise a projector configured to display (e.g., on a screen or wall) the selective and/or attenuation stimuli.

Such a mobile device may be utilized for self-treatment by a subject. For example, the subject may administer a chemical to the subject's blood stream via ingestion or injection and subsequently utilize the mobile drug delivery device to expose himself to the one or more selective stimulus, whereby drug delivery to the desired region(s) of the subject's brain is enhanced. For example, following administering of the chemical to his blood stream, a subject initiates exposure to one or more selective stimulus provided by the mobile device. Should the therapy include attenuation, the mobile device will further comprise attenuation stimuli as described above. After viewing the one or more selective stimulus for a predetermined period of time, the subject may then administer an attenuation agent to the blood stream of the patient (i.e., via ingestion or injection) and, before, during, or after administration of the attenuation agent, the subject may expose himself to the attenuation stimuli via utilization of the mobile device. During the course of therapy/treatment, should the treatment chemical utilized at 120 be altered by the doctor, the mobile device may be updated to provide appropriate selective stimuli suitable to the effects of the new drug and to optionally provide appropriate attenuation stimulus corresponding to stimulation of non-desired area(s) caused by the new selective stimuli.

Such a mobile device may be particularly suitable for therapies such as selective memory erasure, chemotherapy and treatments for addiction, which generally require numerous treatments repeated over time to effect a desired result. For example, due to the debilitating side-effects of chemotherapy, repeated treatment sessions are required to successfully minimize a tumor while maintaining an acceptable health of a subject. The ability of a patient to perform such treatments himself, perhaps at his residence, may enhance the lifestyle of the subject. Additionally, for treatments of addiction, subjects may desire to perform the treatments themselves, rather than having to go to a treatment center where they may be seen by others, such that knowledge of their condition has greater likelihood of remaining private.

EXAMPLES

Example 1

Utilization of Digital Drug Delivery in Treatment of Tumors

Calibration Phase: Reduction of a tumor(s) in a subject having a brain tumor(s) in a region or regions A of his brain may be effected by the following method. One or more selective stimulus is provided which selectively stimulates the region(s) A of the brain of the subject. Such selective stimulus may be provided by determining a set of one or more stimuli which selectively stimulate region(s) A of the brain of the patient. Such selective stimuli may be determined by exposing the subject to a plurality of potential stimuli. The potential stimuli may be auditory, olfactory, visual, gustatory, tactile or a combination thereof. In embodiments, the stimuli are visual. The response of the subject to exposure to the potential stimuli is determined by measuring the blood flow to various regions of the brain of the subject. Blood flow may be measured by fMRI. The effects of the potential stimuli on blood flow to the various regions of the brain are compared, and those potential stimuli that selectively stimulate blood flow to the region(s) A without significantly stimulating other regions of the brain of the patient or those potential stimuli that stimulate area(s) A while stimulating the fewest non-A regions of the brain are categorized as selective stimuli. If desired, attenuation stimuli are provided. Assuming selective stimuli stimulate region(s) A as desired but also undesirably stimulate region(s) B, attenuation stimuli may be determined as those potential stimuli that selectively stimulate region(s) B while not stimulating or while minimally stimulating region(s) A. The effects of the plurality of potential stimuli are thus compared to determine those potential stimuli that selectively activate those areas of the brain undesirably stimulated by the selective stimuli (i.e. region(s) outside region(s) A). Such potential stimuli are categorized as attenuation stimuli.

Once selective stimuli (and attenuating stimuli, if desired) are determined, the stimuli may be packaged in a mobile device as described hereinabove.

Treatment Phase: For treatment, a chemotherapy drug is administered to the subject, either self-administered or administered by another (e.g., by an oncologist). The chemotherapy drug is ingested by the subject or injected directly into the bloodstream of the subject. Ingestion may be more convenient for self-administering of the chemotherapy drug, although injection may be more effective, i.e. may provide more effective/rapid treatment. Following administering of the chemotherapy drug, the subject is exposed to the one or more selective stimulus, for example, by initiating the mobile device. For example, the subject may view a video or slides of selectively stimulating images on a screen (e.g., on a computer monitor or other display) or may flip through a booklet of selectively stimulating images. Due to differences in subject metabolism, the time between administering of the chemotherapy drug via ingestion and exposure to selective stimulus will vary and should be determined in advance, for example, by calculating a drug dose curve with time. Although in general the drug is administered prior to exposure to selective stimuli, exposure to selective stimuli may be initiated prior to, during, or after administering the chemical to the subject.

This may conclude the treatment session in some instances.

Attenuation Phase. Alternatively, an attenuation phase is included in the treatment of the tumor. In such applications, a certain time after completion of exposure of the subject to the one or more selective stimulus, an attenuation agent is administered to the subject (self-administered or administered by another). The attenuation agent is a chemical known to inhibit the effect of and/or degrade the chemotherapy drug. Prior to, during, or after administering the attenuation agent, the subject may be exposed to attenuation stimulus, whereby delivery of the attenuation agent to the non-desired regions of the brain (i.e., non-A region(s) of the brain) that were stimulated by the selective stimuli is enhanced, reducing non-desired effects of the chemotherapy drug on those non-tumor areas of the brain of the subject. As with the selective stimuli, the subject may be exposed to the attenuation stimuli via the mobile drug delivery device. For example, the subject may initiate and/or view a video or slides of attenuation images on a computer or flip through a booklet comprising images of the attenuation images. Exposure to selective and attenuation stimuli may or may not be subject-initiated.

Numerous sessions of treatment phase or treatment and attenuation phases may be carried out over a period of weeks, months, or years, until acceptable tumor reduction is attained.

Example 2

Utilization of Digital Drug Delivery in Treatment of Addiction

Pre-Treatment Phase: Therapy to treat addiction may be effected by the following method. One or more selective stimulus is provided which selectively stimulates pleasure centers in the brain associated with the addiction, for example, images of the addictive substance. These stimuli may also be known as addiction cues. Once selective stimuli are determined, the stimuli may be packaged in a mobile device as described hereinabove.

Treatment Phase. The subject is exposed to (e.g., exposes himself to) addiction cues prior to, during, or after administration of a treatment chemical to the bloodstream of the subject. Exposure can be via the mobile device. The treatment chemical can comprise a dopamine antagonist, whereby treatment seeks to reduce or eliminate the pleasure usually associated with the addiction cues, as neural circuits are no longer being linked to the dopamine reward system. In this manner, the subject may be desensitized to the addiction cues after treatment. Alternatively, the treatment chemical can comprise a chemical that produces an unpleasurable response in the subject, for example norepinephrine and/or emetics, whereby the addiction cues become associated with undesirable results, thus reducing the likelihood that the subject succumbs to the addictive substance/activity in the future.

The treatment phase is repeated numerous times over a period of weeks, months, or years, until desensitization of the subject to the addiction cues is achieved. Utilization of ingested pills to administer the chemical may require longer and/or more numerous treatments sessions to provide adequate desensitization.

Example 3

Utilization of Digital Drug Delivery in Selective Memory Erasure

Pre-Treatment Phase: Selective memory reduction may be effected by the following method. One or more selective stimulus is provided which selectively stimulates region(s) A of the brain of the subject associated with an undesired memory or memories. Such selective stimulus may be provided by determining a set of one or more stimulus which selectively stimulates region(s) A of the brain of the patient. The potential stimuli may be auditory, olfactory, visual, gustatory, tactile or a combination thereof. The selective stimuli may comprise, for example, visual, auditory and/or tactile stimulus revealed by the subject as provoking the undesired memories. The stimuli may all be visual. Once selective stimuli are determined/provided, the selective stimuli may be packaged in a mobile device as described hereinabove.

Treatment Phase: For treatment, cortisol is administered to the subject, either self-administered or administered by another (e.g., a psychiatrist). The cortisol is ingested by the subject or injected directly into the bloodstream of the subject. Ingestion may be more convenient for self-administering of the drug, although injection may be more effective and/or rapid. Prior to, during, or subsequent administering of the cortisol, the subject is exposed to the one or more selective stimulus, for example, via the mobile device. Exposure can comprise initiating and/or watching a video or slides of selectively stimulating images on a computer or by flipping through a booklet of selectively stimulating images. Such exposure enhances delivery of cortisol to areas of the brain associated with the undesired memory(ies). Cortisol will destroy neurons in the Hippocampus and parietal cortex associated with the undesired memories. Due to differences in subject metabolism, the time between administering of the cortisol via ingestion and exposure to selective stimulus will vary and should be determined in advance, for example, by calculating a drug dose curve with time. Although in general the drug is administered prior to exposure to selective stimuli, exposure to selective stimuli may be initiated prior to, during, or after administering the cortisol to the subject.

This may conclude a single treatment session in some instances.

Attenuation Phase. Generally, because cortisol is effectively degraded by the human body, when amounts of cortisol are utilized which do not irreversibly damage the regions of the brain associated with the unwanted memory(ies), no attenuation is needed. In applications, an attenuation phase is included in the selective memory erasure, to prevent irreversible damage to the Hippocampus and/or parietal cortex. In such applications, an excess amount of cortisol is administered to the subject to speed up selective memory erasure and, a certain time after completion of exposure of the subject to the selective stimuli, an attenuation chemical is administered to the subject (self-administered or administered by another). The attenuation chemical is a chemical known to inhibit the effect of and/or degrade the cortisol, thus ensuring that undesirable brain damage is prevented. In such cases, the attenuation stimulus may be substantially identical to the selective stimulus, i.e. may increase the flow of blood to the same or substantially the same target and non-target region(s) to which blood flow is stimulated by the one or more selective stimulus. Alternatively, exposure to attenuation stimuli is not utilized with administering of attenuation agent.

Numerous sessions of treatment phase and/or attenuation phase may be carried out over a period of weeks, months, or years, until suitable selective memory erasure is effected. Utilization of ingested pills to administer the cortisol may require longer and/or more numerous treatments session to provide adequate memory erasure. Utilization of injections of cortisol and/or attenuation chemical may provide faster selective memory erasure. Utilization of excess cortisol injection at 120 with injection of attenuation agent at 140 and/or exposure to attenuation stimulus at 150 may be utilized to speed up memory erasure, requiring shorter and/or fewer treatment sessions.

Example 4

Utilization of DDD in Selective Memory Enhancement

Pre-Treatment Phase: Selective memory enhancement may be effected by the following method. One or more selective stimulus is provided for which a subject would like to have enhanced memory. Such treatment may be desirable, for example, to aid an elderly subject with maintaining a normal life during onset dementia or Alzheimer's. Such selective stimulus may comprise information the subject would like to selectively remember, such as important personal information, including medical requirements/drug dosages, home address, telephone number(s), family or caregiver relationship to the subject, names, telephone numbers, addresses, and the like. Once selective stimuli are determined/provided, the selective stimuli may be packaged in a mobile device as described hereinabove.

Treatment Phase: For treatment, a memory enhancing drug, such as, for example, BDNF and dopamine-enhancing agents including amphetamines, such as Ritalin, is administered to the subject. The memory-enhancing drug may be self-administered or may be administered by another (e.g., a psychiatrist). The memory-enhancing drug is ingested by the subject or injected directly into the bloodstream of the subject. Ingestion may be more convenient for self-administering of the drug, although injection may be more effective and/or rapid. Prior to, during, or subsequent administering of the drug, the subject is exposed to the selective stimulus, via the mobile device, for example. Exposure to selective stimuli focuses delivery of the memory-enhancing drug (at specific concentration) to areas of the brain associated with memory. Exposure can comprise initiating and/or watching a video or slides of selectively stimulating images on a computer or by flipping through a booklet of selectively stimulating images. Such exposure enhances delivery of the drug to areas of the brain associated with memory creation, enhancing memory recall by the patient following treatment. Due to differences in subject metabolism, the time between administering of the drug via ingestion and exposure to selective stimulus will vary and should be determined in advance, for example, by calculating a drug dose curve with time. Although in general the drug is administered prior to exposure to selective stimuli, exposure to selective stimuli may be initiated prior to, during, or after administering the chemical to the subject.

This may conclude a single treatment session in some instances.

Attenuation Phase. Generally, because amounts of memory-enhancing drug may be used and/or the drug is naturally metabolized by the body (e.g. BDNF), an attenuation phase may not be desired. Numerous sessions of treatment phase and/or treatment and attenuation phases may be carried out weekly, monthly, or yearly such that enhanced memory of important information is experienced by the subject.

The above discussion is meant to be illustrative of the principles and various embodiments of the present invention. While embodiments of the invention have been shown and described, numerous variations and modifications thereof can be made by one skilled in the art without departing from the spirit and teachings of the invention. The embodiments described herein are exemplary only, and are not intended to be limiting. Many variations and modifications of the invention disclosed herein will become apparent to those skilled in the art once the above disclosure is fully appreciated. Such variations and modifications are within the scope of the invention and the following claims may be interpreted to embrace all such variations and modifications. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. An apparatus for targeting delivery of a treatment chemical to a target region of the brain of a subject, the apparatus comprising:
    a storage medium on which is stored digital representations of one or more subject-specific selective visual stimuli that selectively stimulate blood flow to the target area of the brain when viewed by the subject; and
    an electronic display device coupled to the storage medium and configured for converting the stored digital representations to images viewable by the eye of the subject;
    wherein the one or more selective visual stimuli were determined by exposing the subject to a plurality of potential stimuli, and then were selected from among the plurality of potential stimuli;
    means for measuring, for each potential stimulus, the blood flow response to multiple regions of the brain of the subject, including the target area and one or more non-target areas; comparing the blood flow responses to the potential stimuli,
    means for selecting based upon and derived from a result generated by said means for measuring as selective stimuli one or more of the potential stimuli that result in relatively more blood flow to the target area and relatively less blood flow to at least one of the one or more non-target areas when the subject is exposed thereto, and
    means for injecting a drug to at least one selected target area during the period of stimulation as determined by the means for selecting;
    wherein the apparatus is further configured, via the electronic display, to present to an eye of the subject one or more attenuation stimuli that selectively stimulate at least one of the one or more non-target areas without substantially stimulating the target area when the subject is exposed thereto,
    wherein the one or more attenuation stimuli are determined by:
    (a) exposing the subject to a potential stimulus;
    (b) determining the response of the subject to the potential stimulus by the means for measuring of the apparatus, wherein determining the response comprises determining the blood flow to the at least one target area and the one or more non-target areas in response to the potential stimulus;
    (c) repeating (a) and (b) for a plurality of potential stimuli; and
    (d) comparing the responses of the subject by the means for measuring of the apparatus to the potential stimuli and selecting as at least one attenuation stimulus, via the means for selecting of the apparatus, one or more of the potential stimuli to which the response determined in (b) was substantial blood flow to at least one of the one or more non-target areas and minimal blood flow to the at least one target area, injected during the period of stimulation.

2. The apparatus of claim 1 wherein the electronic display device comprises a virtual reality system, an AR/VR system, a computer, or any combination thereof.

3. The apparatus of claim 1 wherein measuring the blood flow response to multiple regions of the brain comprises magnetic resonance imaging.

4. The apparatus of claim 1 wherein measuring the blood flow response to multiple regions of the brain comprises functional magnetic resonance imaging, fMRI.

5. The apparatus of claim 1 wherein the apparatus is configured, via the electronic display, for exposing to the eye of the subject the one or more selective visual stimuli that selectively stimulate blood flow to the target are of the brain when viewed by the subject prior to exposing to the eye of the subject the one or more attenuation stimuli.

6. The apparatus of claim 1 wherein the treatment chemical stimulates blood flow to one or more non-target areas of the brain in addition to stimulating blood flow to the at least one target area, and wherein the apparatus further comprises a means for delivering an attenuation agent to the subject, wherein the attenuation agent is a chemical effective to degrade, inhibit, or otherwise minimize the effect of the treatment chemical.

7. The apparatus of claim 1 wherein the medium, the device, or both are portable by the subject.

8. The apparatus of claim 1 further comprising a means of administering a treatment chemical to the blood of the subject.

9. The apparatus of claim 8 wherein the means for administering a treatment chemical to the blood of the subject is selected from pills for ingestion by the subject and syringes for injection of the treatment chemical directly into the blood stream of the subject.

10. The apparatus of claim 1 wherein the target area of the brain of the subject comprises cancerous cells.

11. The apparatus of claim 10 wherein the treatment chemical is selected from chemotherapy drugs.

12. The apparatus of claim 1 wherein the at least one selective stimulus comprises one or more addiction cues and wherein the treatment chemical is selected from the group consisting of dopamine antagonists, stress hormones, and combinations thereof.

13. The apparatus of claim 1 wherein the apparatus, via the electronic display and means for injection, is designed for effecting erasure of one or more undesired memories, wherein the at least one selective stimulus comprises one or more images the subject relates with the one or more undesired memories and wherein the treatment chemical is selected from glucocorticoids.

14. The apparatus of claim 13 wherein the treatment chemical comprises cortisol.

15. The apparatus of claim 13 configured for use with a subject suffering from PTSD.

16. The apparatus of claim 1 wherein the apparatus, via the electronic display and means for injection, is configured for effecting enhanced memory of desired information by the subject, wherein the at least one selective stimulus comprises one or more images of the desired information and wherein the treatment chemical is selected from amphetamines, brain-derived neurotrophic factor (BDNF), and combinations thereof.

17. The apparatus of claim 16 configured for use with a subject suffering from dementia, Alzheimer's, or both.

18. A method of providing a device a suitable for use in the treatment of a brain tumor located in a target area of a brain of a subject, the method comprising:
providing the apparatus of claim 1 to user;
determining, via the apparatus, one or more selective visual stimuli that, when viewed by the subject, selectively stimulate blood flow to the target area of the brain by:
exposing the subject to a plurality of potential stimuli;
measuring, for each potential stimulus, the blood flow response to multiple regions of the brain of the subject, including the target area and a plurality of non-target areas, upon viewing the potential stimulus;
comparing the blood flow response to the exposure to each of the potential stimuli and selecting as the one or more selective visual stimuli one or more of the potential stimuli to which exposure results in relatively more blood flow to the target area while resulting in relatively less blood flow to one or more of the non-target areas;
selecting as selective stimuli based upon and derived from a result generated by said comparing one or more of the potential stimuli that result in relatively more blood flow to the target area and relatively less blood flow to at least one of the one or more non-target areas when the subject is exposed thereto;
injecting a drug to at least one selected target area during the period of stimulation as determined by the means for selecting;
presenting to the eye of the subject one or more attenuation stimuli that selectively stimulate at least one of the one or more non-target areas without substantially stimulating the target area when the subject is exposed thereto, wherein the one or more attenuation stimuli are determined by:
(a) exposing the subject to a potential stimulus;
(b) determining by the apparatus the response of the subject to the potential stimulus by the apparatus, wherein determining the response comprises determining the blood flow to the at least one target area and the one or more non-target areas in response to the potential stimulus;
(c) repeating (a) and (b) for a plurality of potential stimuli; and
(d) comparing the responses of the subject to the potential stimuli and selecting by the device as at least one attenuation stimulus one or more of the potential stimuli to which the response determined in (b) was substantial blood flow to at least one of the one or more non-target areas and minimal blood flow to the at least one target area; injected during the period of stimulation; and
configuring a device to present to the eye of the subject the one or more selective visual stimuli.

19. The method of claim 18 wherein measuring the blood flow response to multiple regions of the brain comprises magnetic resonance imaging.

20. The method of claim 18 wherein viewing of the one or more selective visual stimuli also stimulates blood flow to one or more undesired areas selected from the one or more non-target areas, and wherein the method further comprises:
selecting as one or more visual attenuation stimuli one or more of the potential stimuli that result in relatively more blood flow to at least one of the one or more undesired areas while resulting in relatively less blood flow to the target area; and wherein the device is further configured to present to the eye of the subject the one or more visual attenuation stimuli.

21. A method of selectively delivering a chemical to at least one target area of a brain of a subject, the method comprising:
providing the apparatus of claim 1 to the user;
determining via the apparatus, at least one selective stimulus effective for selectively increasing blood flow to the at least one target area when the subject is exposed thereto;
administering a treatment chemical to the blood of the subject; and
exposing the subject to the at least one selective stimulus, whereby delivery of the treatment chemical to the at least one target area of the brain is enhanced via the increased blood flow stimulated by exposure of the subject to the at least one selective stimulus, further including:

exposing to the eye of the subject the one or more selective visual stimuli that selectively stimulate blood flow to the target are of the brain when viewed by the subject prior to exposing to the eye of the subject the one or more attenuation stimuli, presenting to the eye of the subject one or more attenuation stimuli that selectively stimulate at least one of the one or more non-target areas without substantially stimulating the target area when the subject is exposed thereto, wherein the one or more attenuation stimuli are determined by:
(a) exposing the subject to a potential stimulus;
(b) determining by the apparatus the response of the subject to the potential stimulus,
wherein determining the response comprises determining the blood flow to the at least one
target area and the one or more non-target areas in response to the potential stimulus;
(c) repeating (a) and (b) for a plurality of potential stimuli; and
(d) comparing by the apparatus the responses of the subject to the potential stimuli and selecting as at least one attenuation stimulus one or more of the potential stimuli to which the response determined in (b) was substantial blood flow to at least one of the one or more non-target areas and minimal blood flow to the at least one target area, injected during the period of stimulation;

wherein determining at least one selective stimulus further comprises:
(a) exposing the subject to a potential stimulus;
(b) determining the response of the subject to the potential stimulus, wherein determining the response comprises determining the blood flow to the at least one target area in response to the potential stimulus; injected during the period of stimulation
(c) repeating (a) and (b) for a plurality of potential stimuli; and
(d) comparing the responses of the subject to the potential stimuli and providing as at least one selective stimulus one or more of the potential stimuli to which the response determined in (b) was increased blood flow to the at least one target area.

* * * * *